United States Patent [19]

Astrologes

[11] 4,434,297
[45] Feb. 28, 1984

[54] PROCESS FOR THE PREPARATION OF TRIFLUOROETHANOL

[75] Inventor: Gary W. Astrologes, Hackensack, N.J.

[73] Assignee: Halocarbon Products Corporation, Hackensack, N.J.

[21] Appl. No.: 413,008

[22] Filed: Aug. 30, 1982

Related U.S. Application Data

[63] Continuation of Ser. No. 246,831, Mar. 23, 1981, abandoned.

[51] Int. Cl.$^3$ .................. C07C 67/00; C07C 17/10; C07C 29/09
[52] U.S. Cl. .................................... 560/236; 568/842
[58] Field of Search .................... 560/236; 568/842

[56] References Cited

U.S. PATENT DOCUMENTS

| | | | |
|---|---|---|---|
| 3,239,557 | 3/1966 | Fasick | 260/408 |
| 3,418,360 | 12/1968 | Schulz et al. | 560/236 |
| 3,461,156 | 8/1969 | Fierce | 560/236 |
| 3,968,177 | 7/1976 | Kayhold | 560/236 |

FOREIGN PATENT DOCUMENTS 863190  1/1953  Fed. Rep. of Germany ...... 568/842

OTHER PUBLICATIONS

Fieser et al., Reagents for Organic Synthesis, John Wiley & Sons, New York, (1967), pp. 1–10.

*Primary Examiner*—Howard T. Mars
*Attorney, Agent, or Firm*—Sprung, Horn, Kramer & Woods

[57] ABSTRACT

A process for the preparation of 2,2,2-trifluoroethanol which comprises reacting 2-chloro-1,1,1-trifluoroethane with an alkali metal salt of a carboxylic acid in a substantially anhydrous aprotic solvent thereby to form the carboxylic acid ester of 2,2,2-trifluoroethanol and an alkali metal chloride, reacting the ester with the hydroxide or a basic salt of the alkali metal in water thereby to form 2,2,2-trifluoroethanol and the alkali metal salt of the carboxylic acid, separating the 2,2,2-trifluoroethanol, and recycling the alkali metal salt of the carboxylic acid for further reaction. Advantageously the alkali metal salt is potassium acetate, the aprotic solvent is N-methyl-2-pyrrolidone and the reaction in the N-methyl-2-pyrrolidone is effected at about 150° to 180° C.

9 Claims, No Drawings

PROCESS FOR THE PREPARATION OF TRIFLUOROETHANOL

This is a continuation of application Ser. No. 246,831, filed Mar. 23, 1981 now abandoned.

The present invention relates to a novel process for producing 2,2,2-trifluoroethanol from 2-chloro-1,1,1-trifluoroethane with an ester as an intermediate.

Henne et al in JACS Vol. 70 (1948), page 1968 summarize several processes for producing trifluoroethanol, ultimately favoring reduction of trifluoroacetyl chloride because fusion of 2-chloro-1,1,1-trifluoroethane with postassium acetate at 225° C. followed by saponification gave yields "exceedingly sensitive to the reaction temperature".

German Pat. No. 863,190 discloses reacting trifluoroethyl chloride and potassium acetate above 200° C. and under 80-90 atmospheres of pressure for 40-50 hours, followed by saponification.

Czech Pat. No. 124,981 discloses the same reaction using aqueous high boiling alcohol as solvent, obtaining yields and conversions of about 70% in 60 hours.

U.S. Pat. No. 2,868,846 carries out the same reaction using water or alcohol as solvent with optional addition of acetic acid. The temperature exceeds 200° C. in all examples and the minimum pressure exemplified was 450 psig. In reproducing this process it has been found that at such temperatures the presence of acetic acid produces an unduly corrosive mixture.

It is accordingly an object of the present invention to provide a process for producing trifluoroethanol in high yield and conversion employing only moderate reaction conditions and avoiding corrosive conditions.

This and other objects and advantages are realized in accordance with the present invention pursuant to which there is provided a process for the preparation of 2,2,2-trifluoroethanol which comprises reacting 2-chloro-1,1,1-trifluoroethane with an alkali metal salt of a carboxylic acid in a substantially anhydrous aprotic solvent thereby forming the carboxylic acid ester of 2,2,2-trifluoroethanol and alkali metal chloride, reacting the ester with the hydroxide, carbonate, bicarbonate, or other basic salt of the alkali metal in water thereby to form 2,2,2-trifluoroethanol and the alkali metal salt of the carboxylic acid, separating the 2,2,2-trifluoroethanol, and recycling the alkali metal salt of the carboxylic acid for further reaction.

The alkali metal of the salt of the first step and of the hydroxide or basic salt of the second step is preferably potassium, although sodium also gives good results.

The carboxylic acid of the salt advantageously contains at least two carbon atoms, such as acetic acid, propionic acid, etc., acetic acid being preferred.

The aprotic solvents advantageously are more polar than diethyl ether. Dimethylsulfoxide, dimethylformamide, sulfolane, and dimethylacetamide are representative aprotic solvents but N-methyl-2-pyrrolidone is preferred.

The solvent and reactants should be substantially anhydrous. High water contents lead to increased production of byproducts such as alkali metal fluorides and to a decrease in reaction rate.

The solvent is advantageously present in about 0.5 to 10 and preferably about 1 to 3 times the weight of the potassium acetate. The latter may be employed in approximately equimolar amount with the chlorotrifluoroethane, for example, or either may be present in excess. It has been found suitable to employ the chlorotrifluoroethane in about 1 to 4 times the stoichiometric amount and at the end to separate and recycle unreacted material either directly to the reactor if the process is run continuously or to a reservoir for use in another cycle if run batchwise.

The reaction may be effected at 130° C. but going above 200° C. presents problems of excessive pressures and the like so about 150° to 180° C. is preferred. The pressure, in a batch reaction, may initially be as high as 500 psig due to the highly volatile starting material which it is desired to keep in the liquid phase but it falls rapidly as the reaction progresses. The progress of the reaction can be monitored by the pressure and it can be complete in as little as 2 hours or less up to as much as 25 hours or more although about 5 to 10 hours is a convenient reaction time. Another approach involves adding chlorotrifluoroethane as the reaction proceeds maintaining a fixed pressure or any desired range of pressures.

At the end of the first stage the reactor is cooled and the resulting slurry is filtered to remove the salt, mostly alkali metal chloride although some unreacted alkali metal carboxylic acid salt may also be present. The salt cake may be washed with additional chlorotrifluoroethane or another solvent to remove any remaining organic products. From the liquid filtrate and washings unreacted chlorotrifluoroethane is distilled off, followed by the carboxylic acid ester of trifluoroethanol so as to leave behind the solvent which can be re-used.

The trifluoroethanol ester is then treated with aqueous alkali metal hydroxide or carbonate, bicarbonate, or other alkaline salt to effect saponification in a known manner. The hydroxide may be employed in about 1% to 70% and preferably about 40 to 50% by weight. The saponification can be conducted at room temperature or at elevated temperature, e.g., about 60° to 100° C.

When saponification is substantially complete the desired alcohol is distilled off and a small amount of carboxylic acid may be added just to neutralize any excess hydroxide and to make up for any carboxylic acid salts lost in filtration.

The aqueous solution remaining contains alkali metal carboxylate and it is recycled by distilling off the water, the resulting anhydrous alkali metal carboxylate being ready for further reaction with chlorotrifluoroethane.

The following examples are illustrative of the present invention, all parts being by weight unless otherwise expressed:

EXAMPLE 1

To a stirred slurry of 2.00 mols of potassium acetate in about 320 ml N-methyl-2-pyrrolidone (NMP) in a pressure vessel were added 3.61 mols of $CF_3CH_2Cl$. All the components of this mixture were dried to a water content of 6 parts per million by weight or less. The mixture was then heated to 180° C. As the reaction proceeded the pressure of the reactor vessel fell from its initial maximum of 322 psig. After 26.8 hours the reaction pressure leveled out at 193 psig. The reaction vessel was cooled to near room temperature and the resulting slurry was poured into 1750 ml of water. Analysis of the aqueous layer showed it contained 1.99 moles of potassium chloride (99.5% of theory) and 0.013 moles of potassium fluoride (0.2% loss based on reacted $CF_3CH_2Cl$). The organic layer contained the product ester, NMP, and unreacted $CF_3CH_2Cl$ as its only significant components. Evaporation of a sample overnight showed it contained 0.05% of nonvolatile material.

EXAMPLE 2

A pressure vessel containing 8009 g of powdered potassium acetate was heated to 140° C. and evacuated to a pressure of 0.4 mm Hg for 4 hrs. removing 87 grams of water and acetic acid. To the remaining potassium acetate (7922 g, 80.7 mols) 11,800 g of N-methyl-2-pyrrolidone (NMP) containing 10 parts per million water was added. Then 95 mols of $CF_3CH_2Cl$ containing 62 parts per million water was also added. As the mixture was heated to 180° C., the pressure rose to about 200 pounds per square inch (psig). For the next 4.3 hours, as the pressure dropped, $CF_3CH_2Cl$ was added as necessary to keep the pressure near 200 psig. A total of 14,350 g (121.1 mols) of $CF_3CH_2Cl$ was added to the reactor. After another 6.1 hours at 180° C., the reaction pressure had fallen to 173 psig and appeared to be no longer dropping appreciably. The reaction vessel was cooled to near room temperature and filtered with the filtrate entering a still. The remaining liquid products were washed from the salts on the filter into the still with an additional 65.6 mols of $CF_3CH_2Cl$ leaving behind 69.3 mols of potassium chloride (85.9% conversion of the potassium acetate) and 0.50 mol of potassium fluoride (0.24% loss based on the reacted $CF_3CH_2Cl$). The distillation yielded 111.5 mols of unreacted $CF_3CH_2Cl$ and 66.1 mols of the $CF_3CH_2O_2CCH_3$ leaving behind 11,655 g of dry NMP to be reused.

To the ester combined with that from another batch (79.6 mols total) was added about 84 mols of 45% aqueous potassium hydroxide over 2.5 hours at 70°-75° C. to saponify the ester to 2,2,2-trifluoroethanol and potassium acetate. Following this, acetic acid (3.1 mols) was added to the reactor to neutralize the excess base and the mixture was distilled to yield 78.4 mols $CF_3CH_2OH$ (98.5% of theory). After distillation of most of the water the powdered potassium acetate left behind in the well-stirred reactor was further dried by heating to 140°-155° C. for 5 hours at a pressure of 0.3 mm Hg.

EXAMPLE 3

To 2,2,2-trifluoroethyl acetate (106.7 g, 0.75 mol) heated to 70° to 75° C. was added with stirring over a 6 hour period a solution of 86.1 g (0.62 mol) of potassium carbonate in 86.5 g water (4.8 mols). For an additional 2 hours the mixture was gradually heated to 85° C. After filtration of the precipitated salts, gas chromatography showed the aqueous solution to contain approximately a 99.96:0.04 ratio of 2,2,2-trifluoroethanol to the ester. This high conversion to alcohol using less than an equimolar amount of potassium carbonate plus the presence of dissolved carbon dioxide showed that the ester hydrolysis did not stop with the conversion of the potassium carbonate to potassium bicarbonate, but that this salt reacted further, hydrolyzing more ester and liberating carbon dioxide.

The following table sets forth the data for Examples 1 and 2 (Runs 1 and 6), along with data for other runs. The % conversion has reference to the amount of metal carboxylate reacted as determined by the measured yield of metal chloride. Percent loss was calculated by measuring the amount of MF produced in a competing side reaction in accordance with the equation: $CF_3CH_2Cl + 3MO_2CR \rightarrow 3$ MF + uncharacterized organic products.

| Run | Solvent* | Water Content of solvent (ppm) | Salt | Moles of salt used | Solvent Volume at 25° C., (ml) | Moles of $CF_3CH_2Cl$ | Temperature, (°C.) | Reaction Time, (hrs) | Conversion, (%) | Loss of $CF_3CH_2Cl$ based on KF (or NaF) by-product, (Mole %) |
|---|---|---|---|---|---|---|---|---|---|---|
| 1 | NMP | ≦6 | $KO_2CCH_3$ | 2.0 | 317 | 3.6 | 180 | 26.8 | 99.5 | 0.21 |
| 2 | NMP | ≦6 | $KO_2CCH_3$ | 1.0 | 317 | 3.6 | 180 | 7.8 | 100. | 0.10 |
| 3 | NMP | ≦3 | $KO_2CCH_3$ | 2.0 | 318 | 3.6 | 180 | 10.0 | 94.9 | 0.21 |
| 4 | NMP | 11 | $KO_2CCH_3$ | 2.0 | 317 | 3.6 | 180 | 10.0 | 95.2 | 0.54 |
| 5 | NMP | ≦7 | $KO_2CCH_3$ | 2.0 | 318 | 3.6 | 180 | 10.0 | 96.6 | 0.28 |
| 6 | NMP | 10 | $KO_2CCH_3$ | 80.7 | 11650 | 121.1 | 180 | 10.4 | 85.9 | 0.24 |
| 7 | NMP | 6 | $KO_2CCH_3$ | 2.0 | 317 | 3.6 | 180 | 8.1 | 84.3 | 0.30 |
| 8 | NMP | 200 | $KO_2CCH_3$ | 2.0 | 372 | 3.6 | 180 | 10.3 | 96.9 | 0.25 |
| 9 | NMP | 1000 | $KO_2CCH_3$ | 2.0 | 348 | 3.7 | 177–193 | 10.0 | 95.9 | 0.45 |
| 10 | NMP | 1100 | $KO_2CCH_3$ | 0.46 | 206 | 1.8 | 180 | 2.3 | 100. | 0.54 |
| 11 | NMP | 5 | $KO_2CCH_3$ | 2.0 | 194 | 2.0 | 176–190 | 23.8 | 76. | 0.27 |
| 12 | NMP | 6 | $KO_2CCH_3$ | 2.0 | 317 | 3.6 | 180 | 7.4 | 71.2 | 0.03 |
| 13 | NMP | ≦10 | $KO_2CCH_3$ | 81. | 11050 | 113. | 180 | 9.8 | 65. | 0.13 |
| 14 | NMP | 81 | $KO_2CCH_3$ | 2.0 | 215 | 2.0 | 180 | 8.3 | 59. | ≦0.01 |
| 15 | NMP | 117 | $KO_2CCH_3$ | 2.0 | 471 | 4.0 | 174–188 | 7.6 | 66.5 | 0.12 |
| 16 | NMP | 1100 | $KO_2CCH_3$ | 2.0 | 214 | 2.0 | 180 | 6.0 | 41. | 0.17 |
| 17 | NMP | 1100 | $KO_2CCH_3$ | 0.46 | 203 | 1.8 | 150 | 5.2 | 72. | 0.28 |
| 18 | NMP | 97500 | $KO_2CCH_3$ | 0.46 | 186 | 2.0 | 150 | 1.8 | 13. | 2.1 |
| 19 | NMP | 1100 | $NaO_2CCH_3$ | 0.55 | 204 | 1.6 | 180 | 2.9 | 77. | 0.36 |
| 20 | NMP | 1100 | $NaO_2CCH_2CH_3$ | 0.46 | 202 | 1.8 | 150 | 6.5 | 54. | ≦0.02 |
| 21 | DMA | 121 | $KO_2CCH_3$ | 0.46 | 200 | 1.8 | 150 | 6.2 | 57. | 0.17 |
| 22 | DMF | | $KO_2CCH_3$ | 2.0 | 217 | 2.0 | 200 | 2.6 | 44. | 0.96 |
| 23 | DMF | | $KO_2CCH_3$ | 2.0 | 213 | 2.0 | 170 | 3.1 | 15. | ≦0.1 |
| 24 | DMSO | 1160 | $KO_2CCH_3$ | 0.46 | 148 | 1.5 | 150 | 4.0 | 96. | 0.71 |
| 25 | Sufolane | 64 | $KO_2CCH_3$ | 2.0 | 315 | 3.6 | 180 | 8.1 | 49. | 0.54 |
| 26 | $CH_3CO_2H$ | <1000 | $NaO_2CCH_3$ | 3.0 | 234 | 2.0 | 220–236 | 5. | 10. | 1.8 |
| 27 | $CH_3CO_2H$ | 900000 | $KO_2CCH_3$ | 3.0 | 294 | 1.9 | 230–238 | 6. | 72. | 2.1 |
| 28 | $CH_3CO_2H$ | <1000 | $KO_2CCH_3$ | 3.0 | 180 | 1.8 | 220–230 | 6. | 54.5 | 0.8 |

*NMP = N—Methyl-2-pyrrolidone
DMA = N,N—dimethyl acetamide
DMF = N,N—dimethylformamide
DMSO—Dimethylsulfoxide Runs 27 and 28 show that acetic acid, with or without $H_2O$ added, will work as a solvent but requires high temperatures and pressures (230° C. and 740 psig or higher). Severe corrosion problems were encountered. For example, Run 28 corroded test strips of the following metals (inches/year): nickel, 0.38; 316 stainless steel, 0.069; monel, 0.33; lead, 2.03; carpenter 20, 0.068; silver, 0.0014. The only reasonably resistant metal, silver, is of course expensive.

Run 24 showed that the reaction proceeds rapidly at relatively low temperatures in dimethylsulfoxide, although the solvent decomposes slightly giving odoriferous compounds.

Runs 22 and 23 show that N,N-dimethylformamide is a suitable solvent except that it decomposes somewhat.

Runs 17 and 21 show that under comparable conditions N,N-dimethylacetamide is almost as good a solvent for this reaction as NMP.

Run 25 shows that sulfolane is a suitable solvent for this reaction although it made small amounts of odoriferous by-products.

Runs 19 and 20 show that the sodium salts of acetic and propionic acids react almost as fast as similar reactions with potassium acetate (Runs 10 and 17 respectively). However, this differs from the situation in acetic acid solution where sodium acetate reacts much slower than does potassium acetate (Runs 26 and 28). Suspensions of sodium acetate in NMP have the disadvantage of requiring more NMP to be easily stirrable than do suspensions of potassium acetate.

Runs 1 to 18 demonstrate the favored reaction system using potassium acetate and NMP and chlorotrifluoroethane in varying proportions and conditions. The adverse effects of substantial amounts of water is shown by Run 18 with 9.75% H$_2$O in the NMP. In this run the reaction is relatively slow and seven times as much CF$_3$CH$_2$Cl is lost due to side reactions forming KF than in Run 17 with 1100 ppm H$_2$O in the NMP. No clear effects on the reaction rate were noted upon decreasing the H$_2$O content of the NMP below 1100 ppm. Any further reductions of by-product KF with lower H$_2$O contents were small enough to be masked by other variables.

Runs 11, 14 and 16 show that with equimolar amounts of potassium acetate and chlorotrifluoroethane present, the reaction would not go to completion in a reasonable time (only 76% conversion in 23.8 hours). In contrast, in Runs 1 to 10 conversions of 84 to 100% were achieved in 2.3 to 10 hours by using from 50 to 300% excess chlorotrifluoroethane. Any unreacted CF$_3$CH$_2$Cl can easily be recovered during the distillation of the reaction products.

To demonstrate the low corrosiveness of this reaction in the preferred solvent, test strips of various alloys were present in the reactor in several of the runs. For example, in Run 15 the following corrosion rates were found; carbon steel, 0.01 inch/year; 316 stainless steel, <0.001 inch/year; carpenter 20, <0.001 inch/year.

Other experiments showed that diglyme, which is of very low polarity, was a poor solvent for this reaction and that sodium formate is relatively ineffective as the salt. Water is not a very good medium because even if a quaternary ammonium salt is added to facilitate interphase reaction, the reaction is still very slow unless relatively high temperatures and pressures are used.

It will be understood that the specification and examples are illustrative but not limitative of the present invention and that other embodiments within the spirit and scope of the invention will suggest themselves to those skilled in the art.

What is claimed is:

1. A process for the preparation of 2,2,2-trifluoroethanol which comprises reacting 2-chloro-1,1,1-trifluoroethane with an alkali metal salt of carboxylic acid at least about 130° C. in substantially anhydrous N-methyl-2-pyrrolidone thereby to form the carboxylic acid ester of 2,2,2-trifluoroethanol and alkali metal chloride, reacting the ester with the hydroxide or a basic salt of the alkali metal in water thereby to form 2,2,2-trifluoroethanol and the alkali metal salt of the carboxylic acid and separating the 2,2,2-trifluoroethanol.

2. A process according to claim 1, wherein the carboxylic acid is an aliphatic carboxylic acid having at least 2 carbon atoms.

3. The process according to claim 1, wherein the carboxylic acid is acetic acid.

4. The process according to claim 1, wherein the hydroxide or basic salt of the alkali metal is the hydroxide, carbonate or bicarbonate.

5. The process according to claim 1, wherein the hydroxide or basic salt of the alkali metal is potassium hydroxide.

6. The process according to claim 1, wherein the alkali metal salt is potassium acetate.

7. The process according to claim 1, wherein the alkali metal salt is potassium acetate and it is reacted at about 150° to 180° C.

8. The process according to claim 1, wherein the alkali metal salt of the carboxylic acid is recycled for further reaction.

9. The process which comprises reacting 2-chloro-1,1,1-trifluoroethane with an alkali metal salt of a carboxylic acid at about 130° to 200° C. in substantially anhydrous N-methyl-2-pyrrolidone thereby to form alkali metal chloride and the carboxylic acid ester of 2,2,2-1-trifluoroethanol, and separating the ester from the alkali metal chloride.

* * * * *